US00PP18035P3

(12) United States Plant Patent

Cox et al.

(10) Patent No.: US PP18,035 P3

(45) Date of Patent: Sep. 18, 2007

(54) **'PEACHES AND CREAM': A *GREVILLEA* CULTIVAR**

(50) Latin Name: ***Grevillea* sp.**
Varietal Denomination: Peaches and Cream

(75) Inventors: Denis Eric Cox, Queensland (AU); Janice Evelyn Glazebrook, Queensland (AU)

(73) Assignees: James Walter Carter, Queensland (AU); Riva Lorrraine Carter, Queensland (AU)

( * ) Notice: Subject to any disclaimer, the term of this patent is extended or adjusted under 35 U.S.C. 154(b) by 255 days.

(21) Appl. No.: 10/999,627

(22) Filed: Nov. 30, 2004

(65) Prior Publication Data

US 2006/0117430 P1 Jun. 1, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell

(74) *Attorney, Agent, or Firm*—Saliwanchik, Lloyd & Saliwanchik

(57) ABSTRACT

A new and distinct cultivar of *Grevillea,* named *Grevillea* sp. 'Peaches and Cream', is provided. This plant is characterized by its flower color; two toned color of a cream and pale apricot color, turning darker upon aging.

4 Drawing Sheets

FIELD OF THE INVENTION

A new and distinct cultivar of *Grevillea,* named *Grevillea* sp. 'Peaches and Cream', is provided.

*Grevilla* shrubs and trees come from Australia and are grown for their beautiful fern-like foliage and small tubular flowers. They can grow outside in mild climates such as California. The flowers of these plants grow in clusters at the ends of the branches. They are about half of an inch long and typically come in reds, yellows, or pinks.

The plant of the subject invention is characterized by its flower color; two toned color of a cream and pale apricot color, turning darker upon aging.

*Grevillea* sp. 'Peaches and Cream' looks fantastic in a pot, makes an ideal landscaping plant and is suitable for all size gardens from the biggest to the smallest.

BACKGROUND OF INVENTION

A new seedling arose in a Burpengary, QLD garden bed of Dennis Cox and Janice Glazebrook in 1997. The seedling came up in this garden near a plant of *G. bipinnatifida* and a plant of *G. banksii* white prostrate form. They are the suspected parents. The suspected parent *G. bipinnatifida* is characterized by apricot colored flower, glaucous blue-green leaf and smaller plant height (less than 1 m). The suspected parent *G. banksii* is characterized by cream colored flower, grey-green hairy leaves and procumbent growth habit (up to 0.5 m).

The new plant was watched for about four years. In that time it was grown by cuttings for 3 generations. This plant was selected because it was distinctively different.

BRIEF DESCRIPTION OF THE PHOTOGRAPHS

Figure 1:
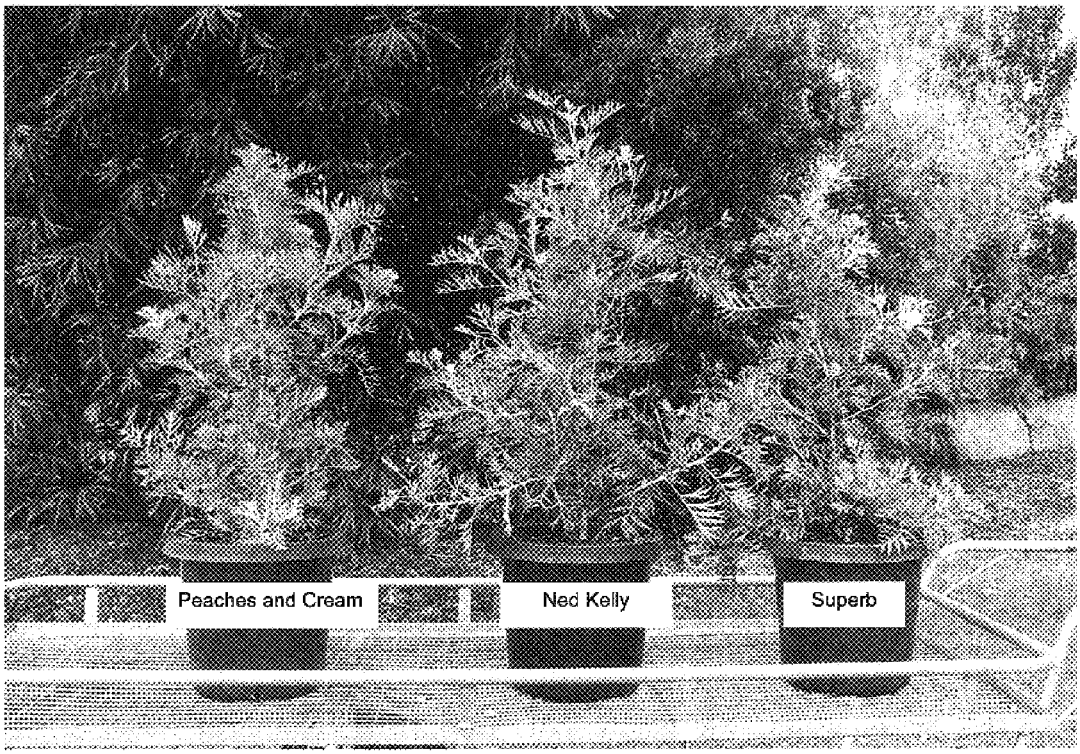

FIG. 1 Photograph comparing three different types of *Grevillea* sp.; 'Peaches and Cream', 'Ned Kelly', and 'Superb'.

Figure 2:
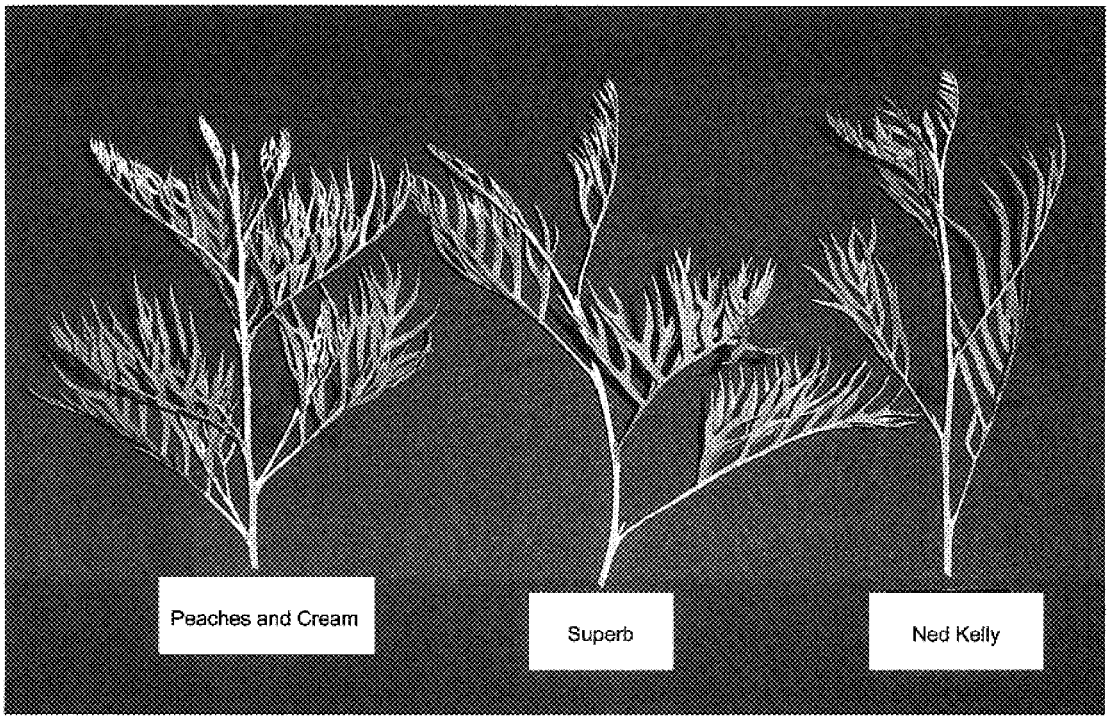

FIG. 2 Photograph comparing three different types of *Grevillea* sp.; 'Peaches and Cream', 'Ned Kelly', and 'Superb'. This photograph is a close up view of the typical leaves of each cultivar.

Figure 3:
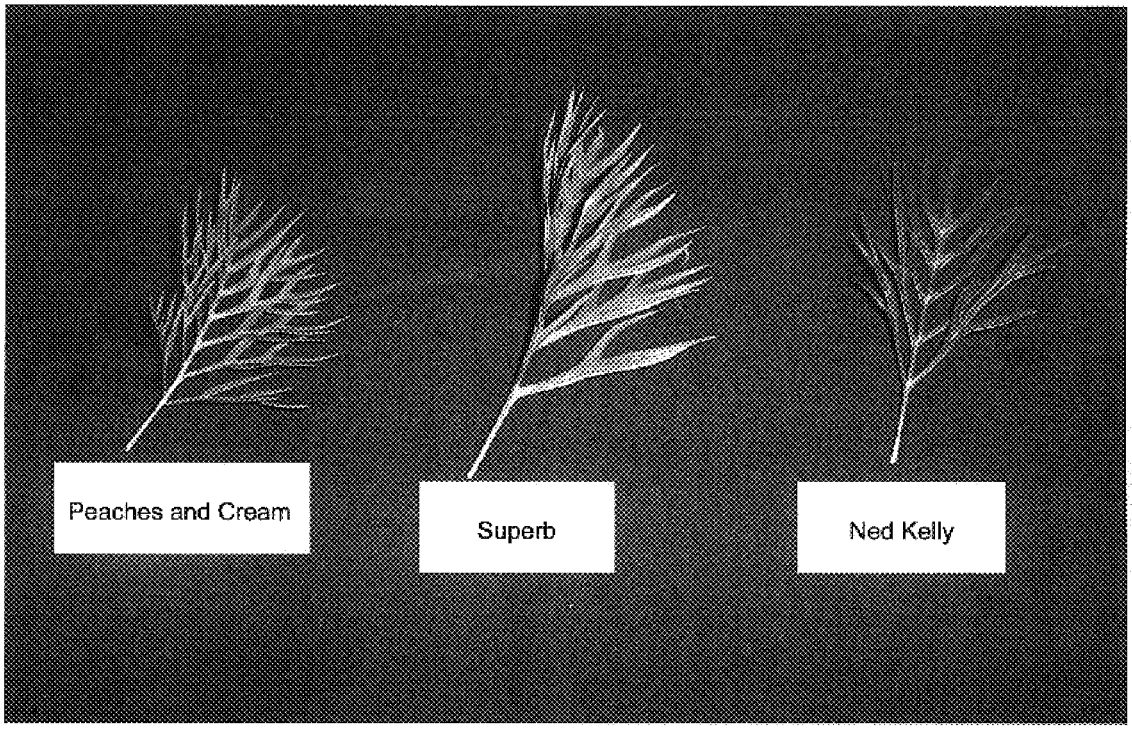

FIG. 3 Photograph comparing three different types of *Grevillea* sp.; 'Peaches and Cream', 'Ned Kelly', and 'Superb'. This photograph is a view of the typical leaves of each cultivar.

Figure 4:
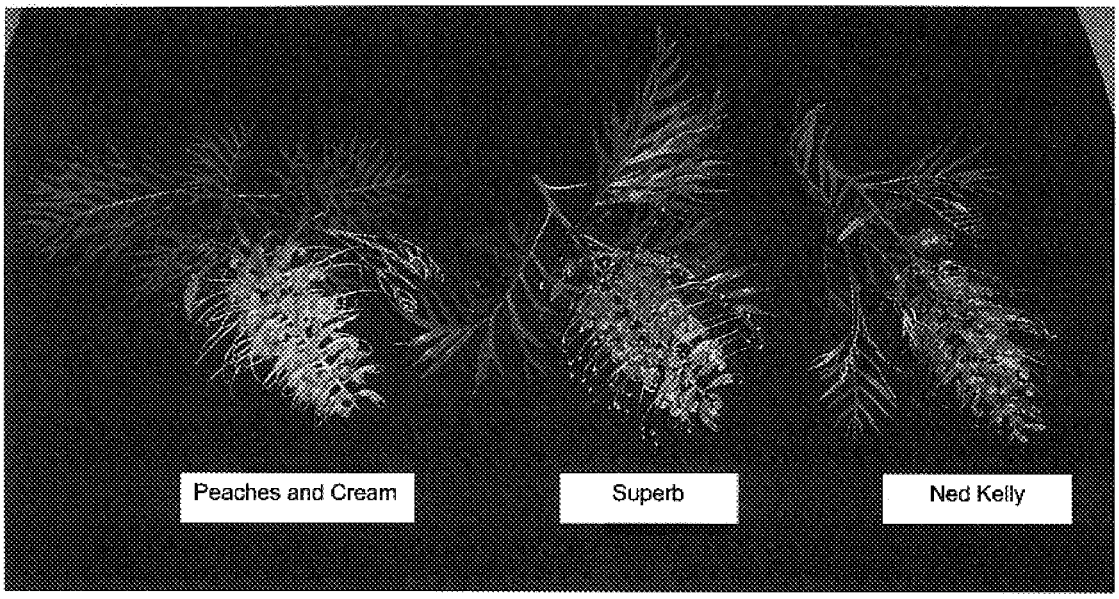

FIG. 4 Photograph comparing three different types of *Grevillea* sp.; 'Peaches and Cream', 'Ned Kelly', and 'Superb'. This photograph is a close up view of the typical blooms of each cultivar.

DETAILED DESCRIPTION OF THE NEW VARIETY

This plant is advantageous in at least the following aspects:

Its attractive foliage
Eye catching flowers
Long flowering period
Bird attracting
Lovely compact shrub
Frost Tolerance
Drought Tolerance
Humidity Tolerance
No reported Pest and Diseases
Lovely bronzy colored foliage over winter Excellent frost tolerance has been reported with the lowest temperature to date being −5° C.

DETAILED BOTANICAL DESCRIPTION

The following observations, measurements and comparisons describe the cultivar grown in Burpengary, QLD in open conditions on a gravel bed. Tube stock of each variety was planted into 200 mm pots of standard bark potting mix.

The age of the observed plants is two years old (one year old from the point the propagated cutting was rooted and potted out).

The following description uses color references to The Royal Horticultural Society Color Chart, 1986, except where general terms of ordinary dictionary significance are used.

Botanical classification: *Grevillea* hybrid cultivar *Grevillea* sp. 'Peaches and Cream'.

Parentage: *G. bipinnatifida* and *G. banksii.*

Original material: Seedling.

Propagation: *Grevillea* sp. 'Peaches and Cream' needs to be reproduced from a cutting to maintain the unique characteristics such as flower, foliage, shape and size.

Plant description:

*Plant size.*—Average height attained about 1.2 m and a width of about 1.5 m.

*Plant shape.*—Naturally bushing shrub growing to a maximum of 2 m high; compact, rounded shape.

*Plant stem.*—Coloration: color of upperside greyed orange (RHS 177B).

*Leaf.*—Mean length: 116.53 mm; mean width: 63.6 mm; divisions of blade: present; degree of division of blade: $2^{nd}$ order; depth of division of blades: sinus greater than two thirds of the way to midrib; number of lobes: 14 to 16; regularity of lobing: irregular, lower 3 or 4 pairs of lobes again divided into 2 to 5 smaller lobes, upper pair of lobes not divided; attitude of longitudinal axis of lobes to the longitudinal axis of midrib: semi-erect; attitude of longitudinal axes of lobes to one another on same side of leaf: parallel; shape of apex of sinus: flattened; width of sinus: broad; shape of lobes: linear; shape of apex of primary and secondary lobes: apiculate; color of upper side of leaf: green (RHS 137A); color of lower side: yellow-green (RHS 147B); midrib: prominent.

*Inflorescence.*—Form: cylindrical; position: terminal or at end of lateral stems; mean length: 104.4 mm; density of florets: dense.

*Perianth.*—Color before anthesis; yellow (RHS 11C); color after anthesis: red (RHS 54C); hairiness: present; overall degree of hairiness: strong; mean tube length: 11 mm.

*Style.*—Color before anthesis: yellow (RHS 11C); color after anthesis: red (RHS 54D); mean length: 39.63 mm.

*Pollen presenter* (*located at the tip of the style and holds pollen*).—Color: orange-red (RHS 34A).

*Ovary.*—Hairiness: present; degree of hairiness: strong.

*Fruit production.*—No fruit production.

*Seed production.*—No seed production.

We claim:

1. A new and distinct cultivar of *Grevillea* plant, named *Grevillea* sp. 'Peaches and Cream' as illustrated and described.

* * * * *